US00PP18124P2

(12) United States Plant Patent
Maycen

(10) Patent No.: US PP18,124 P2
(45) Date of Patent: Oct. 16, 2007

(54) ***VERBENA* PLANT NAMED 'LITTLE ONE'**

(50) Latin Name: *verbena bonariensis*
Varietal Denomination: LITTLE ONE

(76) Inventor: John Andrew Maycen, 2324 Lone Oak La., Vista, CA (US) 92084

( * ) Notice: Subject to any disclaimer, the term of this patent is extended or adjusted under 35 U.S.C. 154(b) by 66 days.

(21) Appl. No.: 11/334,103

(22) Filed: Jan. 17, 2006

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent Bell
*Assistant Examiner*—Annette H Para

(57) ABSTRACT

A new variety of *Verbena* named 'LITTLE ONE' that is characterized by upright habit, small overall size, coarsely textured, dark green foliage, and violet flowers. In combination these traits set 'LITTLE ONE' apart from all other existing varieties of *Verbena* known to the inventor.

2 Drawing Sheets

Genus: *Verbena*. Species: *bonariensis*.
Denomination: 'LITTLE ONE'.

BACKGROUND OF THE INVENTION

The present invention relates to a new and distinct cultivar of Vervain that is grown as an ornamental plant for planter and landscape. The new cultivar is known botanically as *Verbena bonariensis* and will be referred to hereinafter by the cultivar name 'LITTLE ONE'.

'LITTLE ONE' was discovered by the inventor as a naturally occurring individual whole plant mutation, in a commercially grown crop of *Verbena bonariensis* seedlings. The parents are unnamed individual plants of the species *Verbena bonariensis* (unpatented). Discovery of 'LITTLE ONE' occurred in 2004 at the inventor's nursery in Vista, Calif. Selection is based on small overall size when compared to the straight species *Verbena bonariensis*.

The new *Verbena* cultivar 'LITTLE ONE' exhibits upright habit, violet flowers, and coarsely textured dark green foliage. The parent plant, *Verbena bonariensis,* is the closest comparison plant known to the inventor. There are no cultivars of *Verbena bonariensis* known to the inventor. 'LITTLE ONE' is distinguishable from the comparison plant by small overall size. *Verbena bonariensis* reaches 2-meters and 20 cm in height at maturity. The new cultivar 'LITTLE ONE' is 38 cm in height the first year, and grows to no more than 50 cm in height and 50 cm in width when fully established. 'LITTLE ONE' is known to the inventor to be long-lived when compared to *Verbena bonariensis*.

The first asexual reproduction of 'LITTLE ONE' was conducted by the inventor in 2004 at the inventor's nursery in Vista, Calif. The method used for asexual propagation was softwood cuttings. The inventor determined that the characteristics of the new *Verbena* cultivar 'LITTLE ONE' as stable and are reproduced true to type in successive generations of asexual reproduction.

SUMMARY OF THE INVENTION

The following traits have been repeatedly observed and represent the characteristics of the new *Verbena* cultivar 'LITTLE ONE'. These traits in combination distinguish 'LITTLE ONE' from all other commercial varieties of *Verbena bonariensis* known to the inventor. 'LITTLE ONE' has not been tested under all possible conditions and phenotypic differences may be observed with variations in environmental, climatic and cultural conditions, however, without any variance in genotype.

1. *Verbena bonariensis* 'LITTLE ONE' exhibits upright habit.
2. *Verbena bonariensis* 'LITTLE ONE' is small in overall size when compared to the straight species.
3. *Verbena bonariensis* 'LITTLE ONE' exhibits violet flower heads.
4. *Verbena bonariensis* 'LITTLE ONE' is sterile.
5. *Verbena bonariensis* 'LITTLE ONE' is 50 cm is height and 50 cm in width at maturity.
6. *Verbena bonariensis* 'LITTLE ONE' exhibits coarsely textured dark green foliage.
7. *Verbena bonariensis* 'LITTLE ONE' grows well in full sun or partial shade, planted in average to poor well-drained soil, and given regular water.
8. *Verbena bonariensis* 'LITTLE ONE' is readily propagated using softwood cuttings.
9. *Verbena bonariensis* 'LITTLE ONE' is an ornamental recommended for use in planters and as a border plant in the landscape.
10. *Verbena bonariensis* 'LITTLE ONE' is hardy in USDA Zone 7.

BRIEF DESCRIPTION OF THE DRAWINGS

The accompanying drawings illustrate the overall appearance of the new *Verbena* plant 'LITTLE ONE' showing colors as true as it is reasonably possible to obtain in colored reproductions of this type. Colors in the drawings may differ from the color values cited in the detailed botanical description, which accurately describe the actual colors of the new variety *Verbena bonariensis* 'LITTLE ONE'.

The drawing labeled

The drawing labeled

Figure 1:
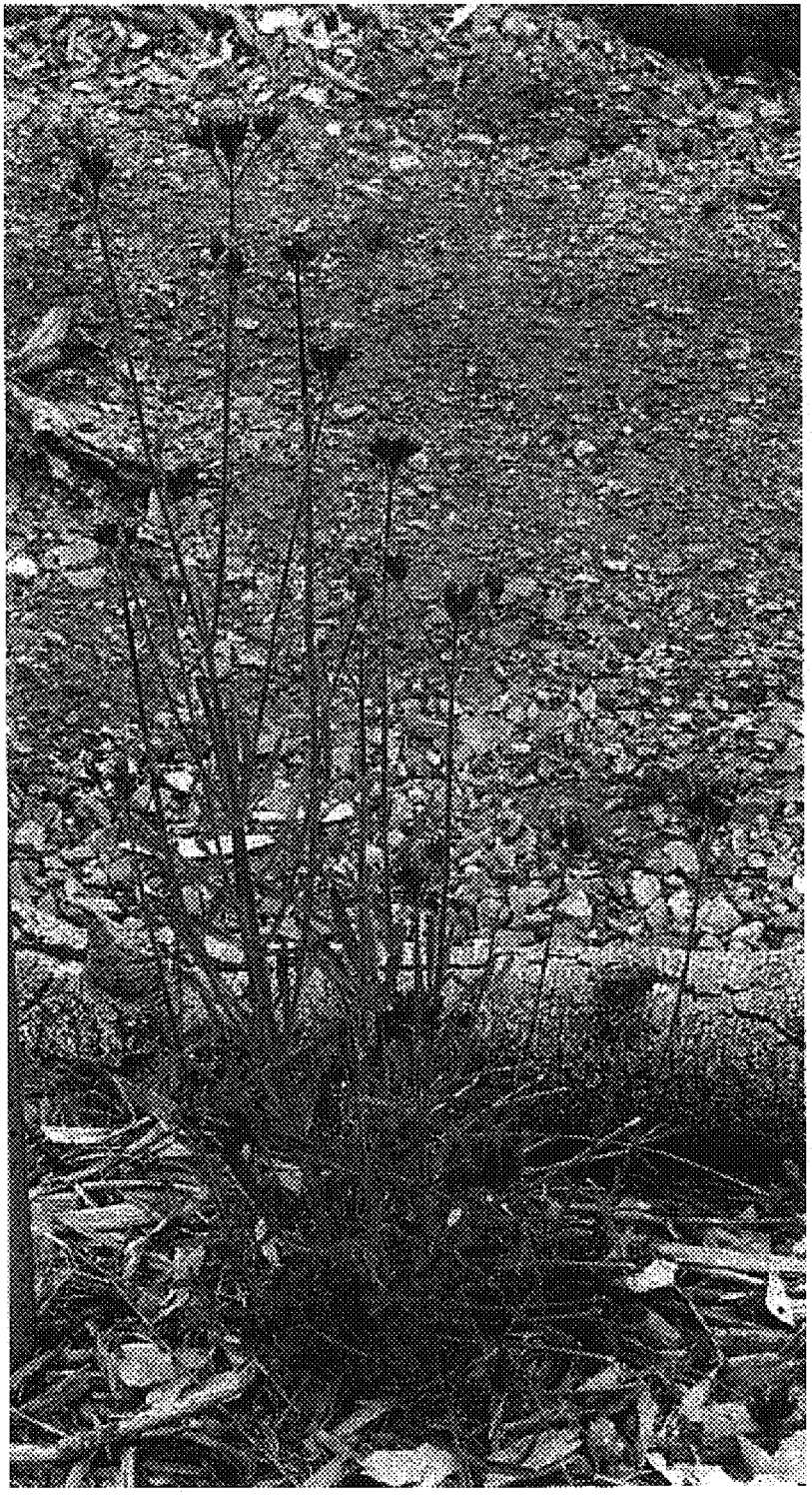
FIG. 1 depicts the entire plant in bloom from a side perspective.
Figure 2:
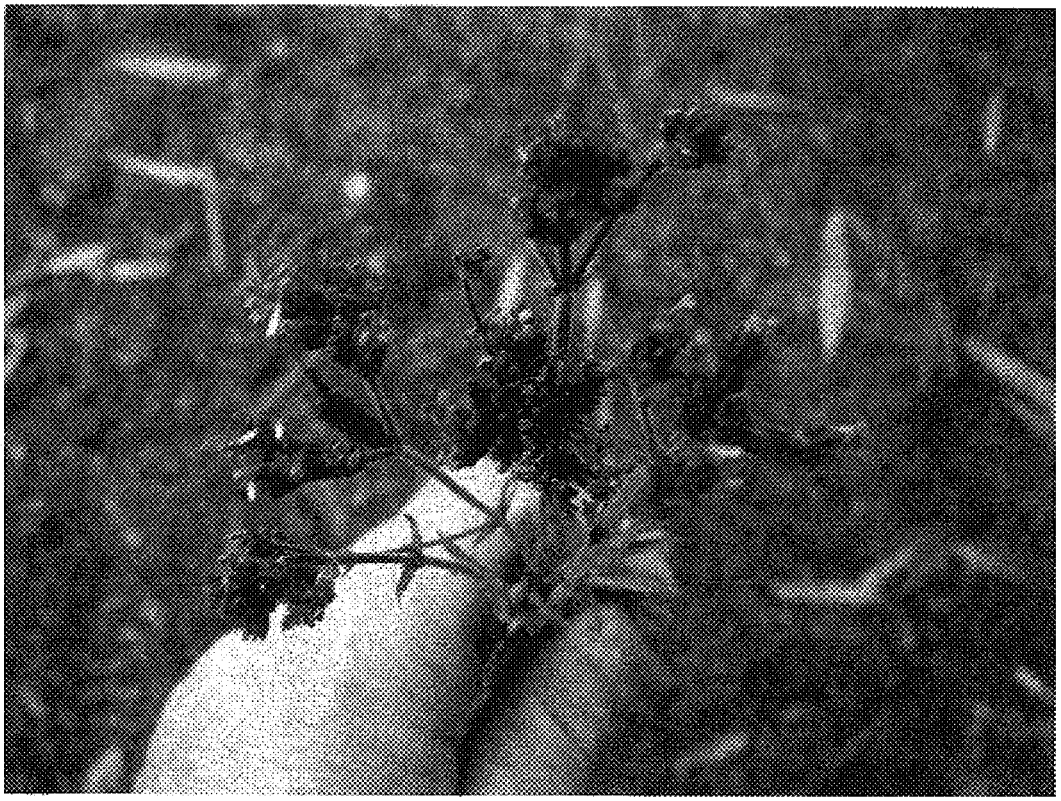
FIG. 2 depicts a close-up view of the flower.

The drawings were made using conventional techniques and although colors may appear different from actual colors due to light reflectance they are as accurate as possible by conventional photography.

BOTANICAL DESCRIPTION OF THE PLANT

The following is a detailed description of *Verbena* 'LITTLE ONE' as grown in a 2-liter-container out-of-doors in Arroyo Grande, Calif. The color determinations are in accordance with the 2001 Royal Horticultural Society Colour Chart of London, England, except where general color terms of ordinary dictionary significance are used. Growing requirements are similar to the species.

Botanical classification: *Verbena bonariensis* 'LITTLE ONE'.
Genus: *Verbena.*
Plant species: *bonariensis.*
Denomination: 'LITTLE ONE'.
Common name: Vervain.
Commercial classification: Herbaceous perennial.
Plant use: Ornamental for planter, or border plant in the landscape.
Recommended commercial container size: 2-liter commercial container.
Plant dimensions: 38 cm in height and 50 cm in width in a 2-liter container after one year.
Plant dimensions at maturity: 50 cm in height and 50 cm in width at maturity.
Cultural requirements: Plant in full sun or partial shade in any average to poor well-draining soil, with regular watering.
Special needs: No special needs known to the inventor.
Pests and disease susceptivility: None known to the inventor.
Disease resistance: None known to the inventor.
Parentage: *Verbena bonariensis* 'LITTLE ONE' was discovered as a naturally occurring individual whole plant mutation in a commercially grown crop of *Verbena bonariensis* seedlings:
*Female parent.*—An individual *Verbena bonariensis.*
*Male parent.*—An individual *Verbena bonariensis.*
Bloom period: Spring, summer and fall.
Plant habit: Upright habit.
Vigor: Moderate vigor.
Hardiness: USDA Zone 7.
Root system: Fine and fibrous.
Propagation: Propagation is accomplished by using softwood cuttings.
Time to develop roots: 2–3 weeks is needed for initial cuttings to develop roots.
Crop time: Time needed to produce a finished 2-liter container ranges from 4–5 months.
Stem:
*Stem shape.*—Tetragonal.
*Stem color.*—Colors 137A and 59A are individually present on an individual stem.
*Stem dimensions.*—An individual stem is 36 cm in length and ranges from 1.75 mm. to 3 mm. in diameter.
*Stem surface.*—Heavily stipitate glandular.
*Stem surface appearance.*—Glossy.
*Lateral stem dimensions.*—An individual lateral stem is 7 cm in length and 1.75 cm in diameter.
*Stem texture.*—Viscid.
*Stem strength.*—Brittle.
*Branching.*—Divergentg.
*Internode length.*—3 cm between nodes.
Foliage:
*Leaf type.*—Evergreen.
*Leaf arrangement.*—Decussate-opposite arrangement.
*Leaf quantity.*—Quantity ranges from 36 to 42 leaves per individual stem.
*Leaf shape.*—Gladiate.
*Leaf margins.*—Sparsely crenate.
*Leaf apex.*—Acute.
*Leaf base.*—Truncate.
*Leaf division.*—Simple.
*Leaf venation pattern.*—Pinnate.
*Leaf texture* (*adaxial and abaxial surfaces*).—Coarse.
*Attachment.*—Sessile.
*Leaf surface* (*abaxial surface*).—Canescent.
*Leaf surface* (*adaxial surface*).—Hispid.
*Leaf length.*—Leaf ranges from 1.50 cm to 7 cm in length on an individual stem.
*Leaf width.*—Leaf ranges from 4 mm. to 0.75 cm in width on an individual stem.
*Leaf color* (*adaxial surface*).—147A.
*Leaf color* (*abaxial surface*).—137B.
*Fragrance.*—None observed.
Flowers:
*Inflorescence type.*—Broad corymb.
*Inflorescence dimensions.*—An individual inflorescence ranges from 2.50 cm to 3 cm in diameter, and 2.50 cm in depth, on an individual 2-liter container plant.
*Persistent or self-cleaning.*—Persistent.
*Flower bud shape.*—Globose in shape.
*Flower bud color.*—N82A.
*Flower bud dimensions.*—An individual flower bud is 1 mm. in length and 1 mm. in diameter.
*Quantity of flowers per inflorescence.*—An average of 15 individual flowers per individual inflorescence.
*Flower aspect.*—Facing upward and outward.
*Flower dimensions.*—An individual flower is 9 mm. in depth and 4 mm. in diameter.
*Flower shape.*—Salverform in shape.
*Flower color.*—Colors 59A, N82A, and N82D are individually present on an individual flower.
*Corolla tube depth.*—6 mm in depth.
*Corolla tube diameter.*—1.20 mm in diameter.
*Shape of corolla tube.*—Cylindrical in shape.
*Corolla tube surfaces* (*ventral and dorsal surfaces*).—Pubescent.
*Color of hairs.*—156C.
*Corolla tube color* (*ventral surface*).—59A.
*Corolla tube color* (*dorsal surface*).—59A.
*Petals.*—Five in number.
*Petal color* (*adaxial surface*).—N82A.
*Petal color* (*abaxial surface*).—N82D.
*Petal apex.*—Emarginate.
*Petal margin.*—Entire.
*Petal surfaces* (*adaxial and abaxial surfaces*).—Glabrous surfaces.
*Petal appearance* (*adaxial and abaxial surfaces*).—Irridescent.
*Petals fused or unfused.*—Fused.
*Petal dimensions.*—1.50 cm in width and 1.75 in length.

*Calyx.*—An individual calyx ranges from imbricate to gamosepalous on an individual 2-liter container plant.

*Calyx dimensions.*—9 mm. in length and 7 mm. in width.

*Calyx color.*—Colors 147B and 59A are individually present on an individual calyx.

*Calyx surface.*—Pubescent.

*Sepals.*—15–20 in number.

*Sepal dimensions.*—An individual sepal is 3 mm. in length and 0.75 mm. in width.

*Sepal apex.*—Acute.

*Sepal base.*—Truncate.

*Fused or unfused.*—Sepals are fused into a cluster.

*Sepal color.*—Colors 147B and 59A are individually present on an individual sepal.

*Pedicel length.*—6 mm.

*Pedicel surface.*—Pubescent.

*Pedicel color.*—137A.

*Peduncle length.*—Peduncle ranges from 5–16 cm in length.

*Peduncle width.*—Peduncle is 2 mm. in width.

*Peduncle surface.*—Hispid.

*Peduncle appearance.*—Glossy.

*Peduncle color.*—147A.

*Flower fragrance.*—Slightly sweet scent.

Reproductive organs:

*Stamens.*—Stamens range from 0–1 in number per individual flower.

*Stamen color.*—162A.

*Stamen dimensions.*—An individual stamen is 2 mm. in length.

*Anther dimensions.*—An individual anther is 0.20 mm. in length and less than 0.20 mm. in width.

*Anther color.*—161A.

*Pollen.*—None observed.

*Pistil.*—None observed.

*Ovary.*—None observed.

Seed: None observed. 'LITTLE ONE' is sterile.

It is claimed:

1. A new and distinct cultivar of *Verbena* plant named 'LITTLE ONE' as described and illustrated herein.

* * * * *